US008525667B2

(12) United States Patent
Lin et al.

(10) Patent No.: US 8,525,667 B2
(45) Date of Patent: Sep. 3, 2013

(54) SICK SIGNAL, EMBEDDED INTELLIGENT CONTINUOUS PULSE MONITOR AND MONITORING METHOD THEREOF

(76) Inventors: Sung-Lien Lin, Yilan (TW); Shang-Ting Lin, Yilan (TW)

(*) Notice: Subject to any disclaimer, the term of this patent is extended or adjusted under 35 U.S.C. 154(b) by 544 days.

(21) Appl. No.: 12/756,479

(22) Filed: Apr. 8, 2010

(65) Prior Publication Data
US 2011/0156912 A1 Jun. 30, 2011

(30) Foreign Application Priority Data

Dec. 31, 2009 (TW) ................................ 98146066 A

(51) Int. Cl.
*G08B 1/08* (2006.01)
(52) U.S. Cl.
USPC ............ 340/539.12; 340/573.1; 340/573.6; 600/301; 600/481; 482/8
(58) Field of Classification Search
USPC ............... 600/481–528, 301; 340/539.12, 340/573.1, 573.6, 571, 571.2, 572.4, 572.7, 340/572.8; 128/900, 903, 923; 377/28–31, 377/50
See application file for complete search history.

(56) References Cited

U.S. PATENT DOCUMENTS

| 5,733,259 A | * | 3/1998 | Valcke et al. ................. 604/66 |
| 2008/0266118 A1 | * | 10/2008 | Pierson et al. ............. 340/573.6 |

OTHER PUBLICATIONS

Nellcor Puritan Bennett, "Nellcor Symphony N-3000 Pulse Oximeter Operators Manual", 1997, p. 45-46.*

* cited by examiner

*Primary Examiner* — Brian Zimmerman
*Assistant Examiner* — Laura Nguyen

(57) ABSTRACT

A sick signal, embedded intelligent continuous pulse monitor and monitoring method thereof is covered by a flexible material so that the flexible material is fitted to a pulse's position of a human body (such as wrist or ankle) and comprises: a processing unit connected with a pulse detecting unit to receive a pulsing frequency of an artery; at least one control unit to control and transmit a signal to the processing unit to be calculated; at least one display unit to receive a processed signal via the processing unit and display the processed signal; a signal transmitting unit connected with the processing unit to transmit the processed signal to an external device. Moreover, when the pulse is over a predetermined value in response to actual age of the patient, the display unit makes warning signal to provided related information to the patient or caregiver.

1 Claim, 5 Drawing Sheets

SICK SIGNAL, EMBEDDED INTELLIGENT CONTINUOUS PULSE MONITOR AND MONITORING METHOD THEREOF

BACKGROUND OF THE INVENTION

1. Field of the Invention

The present invention relates to a sick signal, embedded intelligent continuous pulse monitor device and monitoring method thereof to detect a pulsing frequency of an artery precisely by being fitted to a wrist or ankle.

2. Description of the Prior Art

A patient is monitored by using heart rhythm to display pulsing frequency and diagram, however, such a device is only read by medical personnel. Besides, the pulsing frequency is higher or lower in different conditions that can not be applied in care or nursing field.

The present invention has arisen to mitigate and/or obviate the afore-described disadvantages.

SUMMARY OF THE INVENTION

The primary object of the present invention is to provide a sick signal, embedded intelligent continuous pulse monitor and monitoring method thereof that is used to reveal illness such as significant fever by monitoring abnormally increasing and decreasing heart rate.

A further object of the present invention is to provide a sick signal, embedded intelligent continuous pulse monitor and monitoring method thereof that is used in home care field easily and automatically calibrated based on user's condition.

Another object of the present invention is to provide a sick signal, embedded intelligent continuous pulse monitor and monitoring method thereof that is portable easily, precise, economical and make a warning signal if a measuring pulsing is over a normal value.

A sick signal, embedded intelligent continuous pulse monitor and monitoring method thereof in accordance with a preferred embodiment of the present invention is covered by a flexible material so that the flexible martial is fitted to a pulse's position of a human body and comprises a processing unit, a pulse detecting unit, a control unit, a display unit, and a signal transmitting unit, wherein before applying the sick signal, embedded intelligent continuous pulse monitor to sense a pulsing frequency of an artery of the human body, the control unit (such as a control key) is inputted patient's age, and then the pulse detecting unit detects and transmits the pulsing frequency of the artery to the processing unit to be calculated. If the pulsing frequency is more than or less than a set value, the display unit (such as an indicator light, buzzer or display screen) displays a warning signal to notice a patient or caregiver. Besides, the signal transmitting unit (such as infrared ray module, bluetooth module, wireless network module, wireless network protocol module, or wireless radio frequency identifier) transmits the message to an external device so as to monitor patient's status by the caregiver.

DETAILED DESCRIPTION OF THE PREFERRED EMBODIMENTS

The present invention will be clearer from the following description when viewed together with the accompanying drawings, which show, for purpose of illustrations only, the preferred embodiment in accordance with the present invention.

Figure 1:
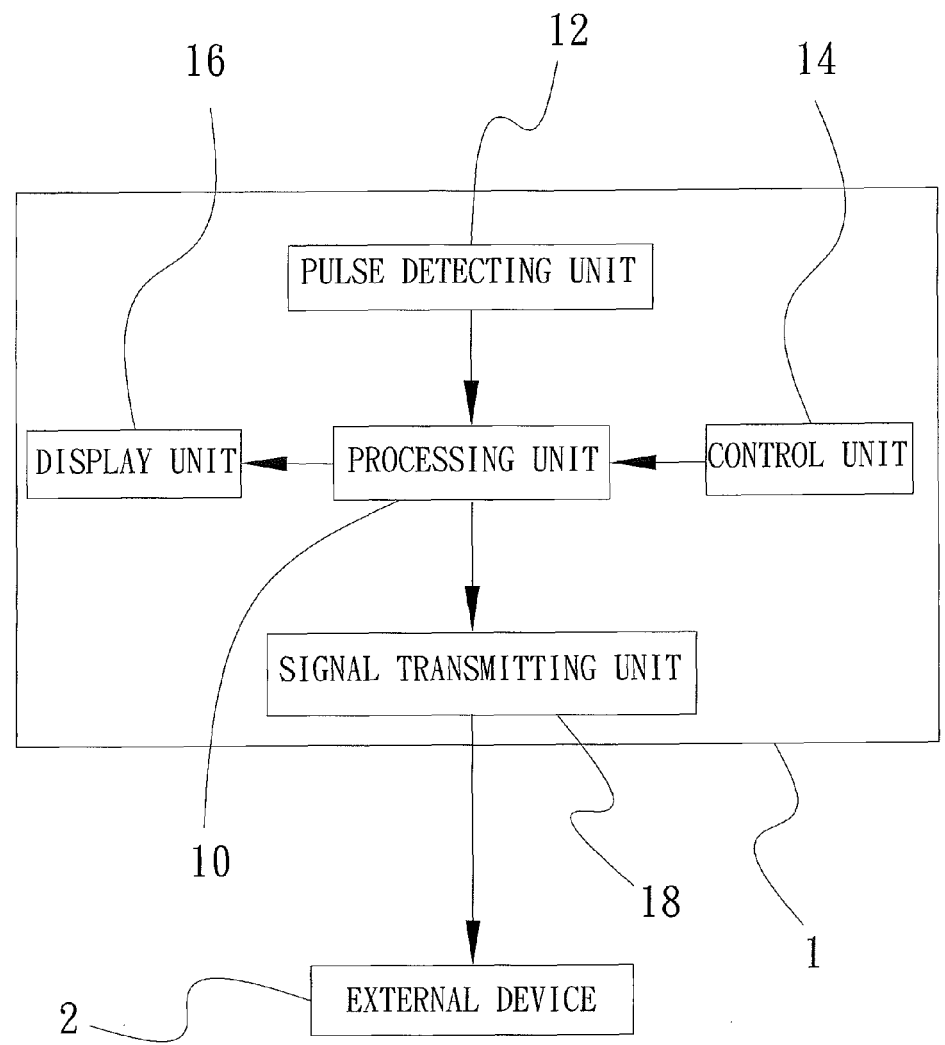
FIG. 1 is a block diagram showing the operation of a sick signal, embedded intelligent continuous pulse monitor according to a preferred embodiment of the present invention.
Figure 2:
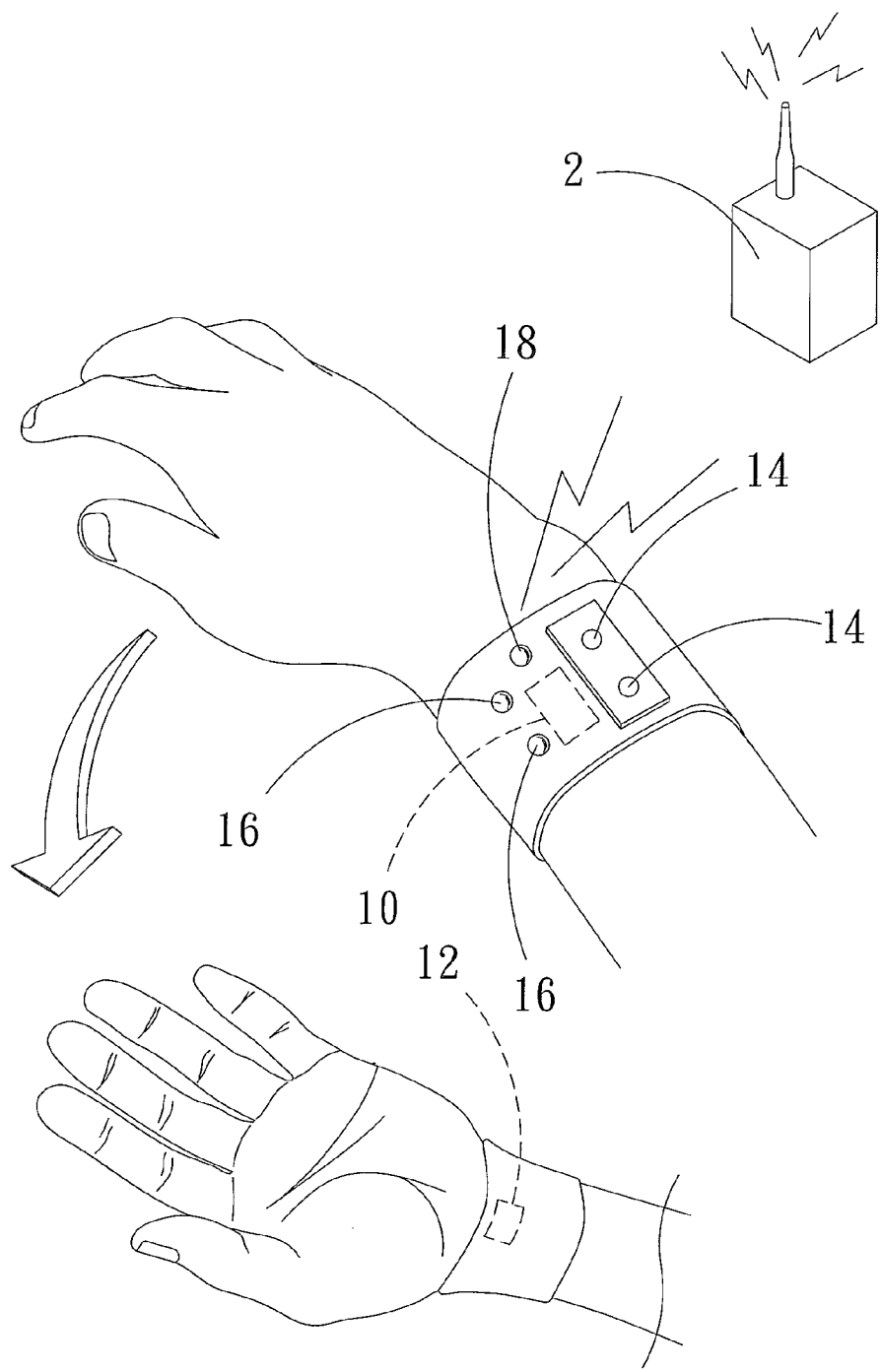
FIG. 2 is a perspective view showing the sick signal, embedded intelligent continuous pulse monitor being fitted to a user's wrist.

Referring to FIGS. 1 and 2, a sick signal, embedded intelligent continuous pulse monitor 1 in accordance with a preferred embodiment of the present invention is covered by a flexible material so that the flexible material is fitted to a pulse's position of a human body (including wrist or ankle) and comprises a processing unit 10, a pulse detecting unit 12, a control unit 14, a display unit 16, and a signal transmitting unit 18, wherein before applying the a sick signal, embedded intelligent continuous pulse monitor 1 to sense a pulsing frequency of an artery of the human body, the control unit 14 (such as a control key) is inputted patient's age, and then the pulse detecting unit 12 detects and transmits the pulsing frequency of the artery to the processing unit 10 to be calculated. If the pulsing frequency is 1-30 pulses more than or less than a set value, the display unit 16 (such as an indicator light, buzzer or display screen) displays a warning signal to notice a patient or caregiver. Besides, the signal transmitting unit 18 (such as infrared ray module, bluetooth module, wireless network module, wireless network protocol module, or wireless radio frequency identifier) transmits the message to an external device 2 so as to monitor patient's status by the caregiver.

Figure 3:
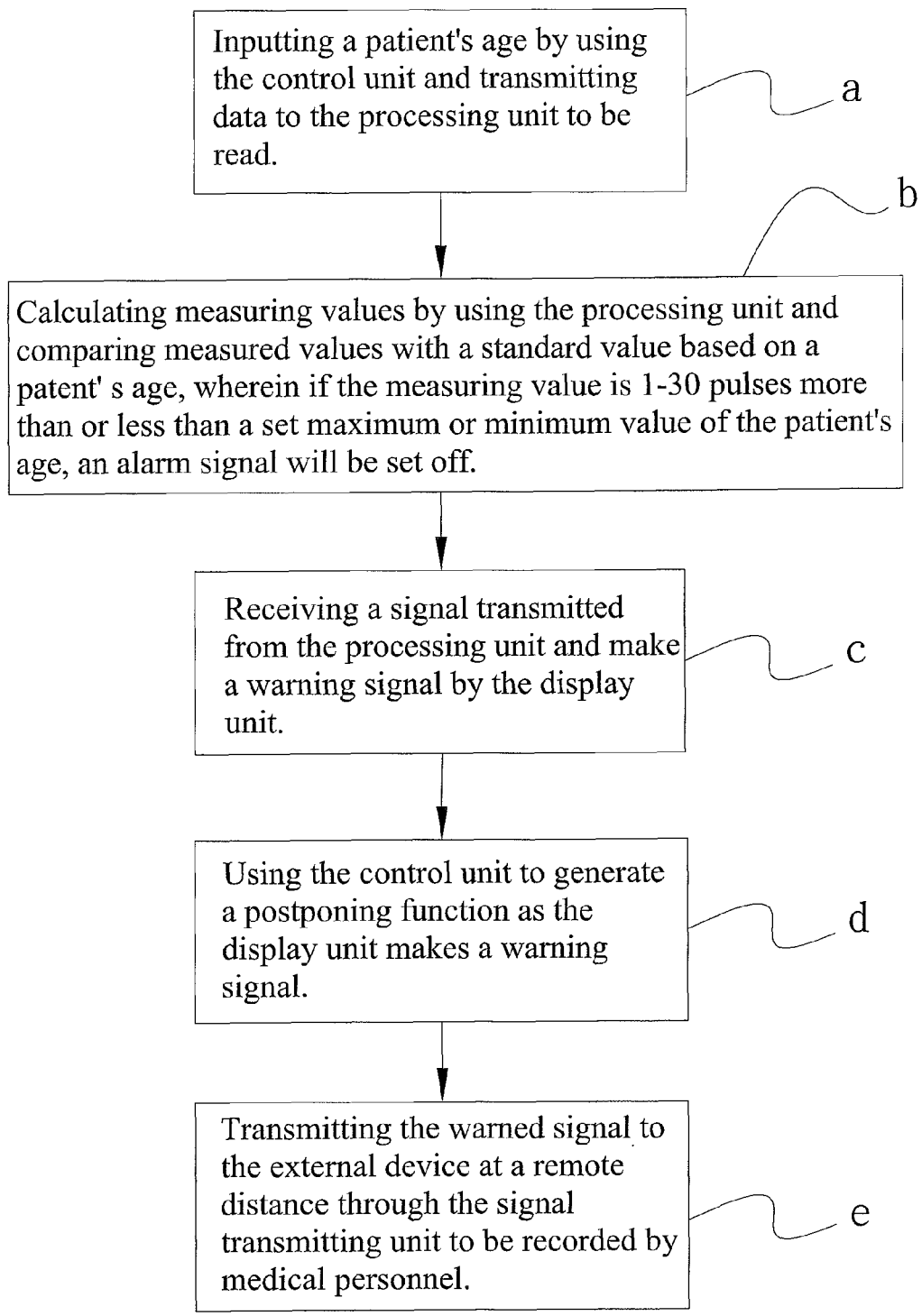
FIG. 3 is a flow chart showing the set steps of the sick signal, embedded intelligent continuous pulse monitor being used to a general patient.

As shown in FIG. 3, the steps of operating the sick signal, embedded intelligent continuous pulse monitor 1 are listed as follows:

a. inputting a patient's age by using the control unit 14 and transmitting data to the processing unit 10 to be read;

b. calculating measuring values by using the processing unit 10 and comparing measured values with a standard value based on a patient's age, wherein if the measuring value is 1-30 pulses more than or less than a set maximum or minimum value of the patient's age, an alarm signal will be set off;

c. receiving a signal transmitted from the processing unit 10 and making a warning signal by the display unit 16;

d. using the control unit 14 to generate a postponing function as the display unit 16 makes a warning signal;

e. transmitting the warned signal to the external device 2 at a remote distance through the signal transmitting unit 18 to be recorded by medical personnel.

Therefore, after the user inputs the data (such as a birthday of the patient) by ways of the control unit 14, a user interface having only one control key unit without any figures and number so as to be read easily by any user, the processing unit 10 arranges within a certain zone (more than or less than a standard value) of heart beating according to patient's age, and when an abnormal status happens, the sick signal, embedded intelligent continuous pulse monitor 1 reflects as follows:

If one of measuring values increases to 1-30 beats/per minute (bpm) more than age related heart rate limit (maximum value) or decreases to 1-30 beats/per minute less than age related heart rate limit (minimum value), the display unit 16 is started to alarm. Therefore, the caregiver can check the patient's status. In the meantime, the caregiver or the user presses the control unit 14 once more so as to obtain a new maximum or minimum value temporarily, this is so called a postpone phenomenon.

The mechanisms are the following:

1. when one of the measuring values of the individual patient is more than maximum value, the control unit 14 is pressed so that the sick signal, embedded intelligent continuous pulse monitor automatically adds 1-50 bpm according to measuring value, thereby increasing that maximal measuring value of the patient temporarily, when one of the measuring values of the individual patient is less than a minimum value, the control unit 14 is pressed so that the sick signal, embedded intelligent continuous pulse monitor automatically reduces 1-30 bpm according to measuring value, thereby decreasing that minimal measuring value of the patient temporarily. And the temporary normal maximum and minimum values can be kept during a tolerant term of 1-5 hours so that a treatment (such as a fever bring-down treatment) is processed by the medical personnel, caregiver or the user. Thereafter, a correspond value in the monitor zone returns original set standard, therefore as the display unit 16 displays a warning signal, the signal transmitting unit 18 transmits the warning signal to the external device 2 at a remote distance to be recorded by other caregivers.

2. Furthermore, a warning loop is installed in the sick signal, embedded intelligent continuous pulse monitor 1 is started, if a warning signal is not made or the control unit 14 is not operated, the sick signal, embedded intelligent continuous pulse monitor 1 automatically calculates an average of the pulsing frequency during 0-240 minutes to be a basic frequency. Thereafter, if the certain measuring value is higher than 2-30% of basic frequency or lowers than 5-80% of basic frequency, the display unit 16 is started, and the user presses the control unit 14 to obtain the tolerant term and the temporary standard as above-mentioned.

Figure 4:
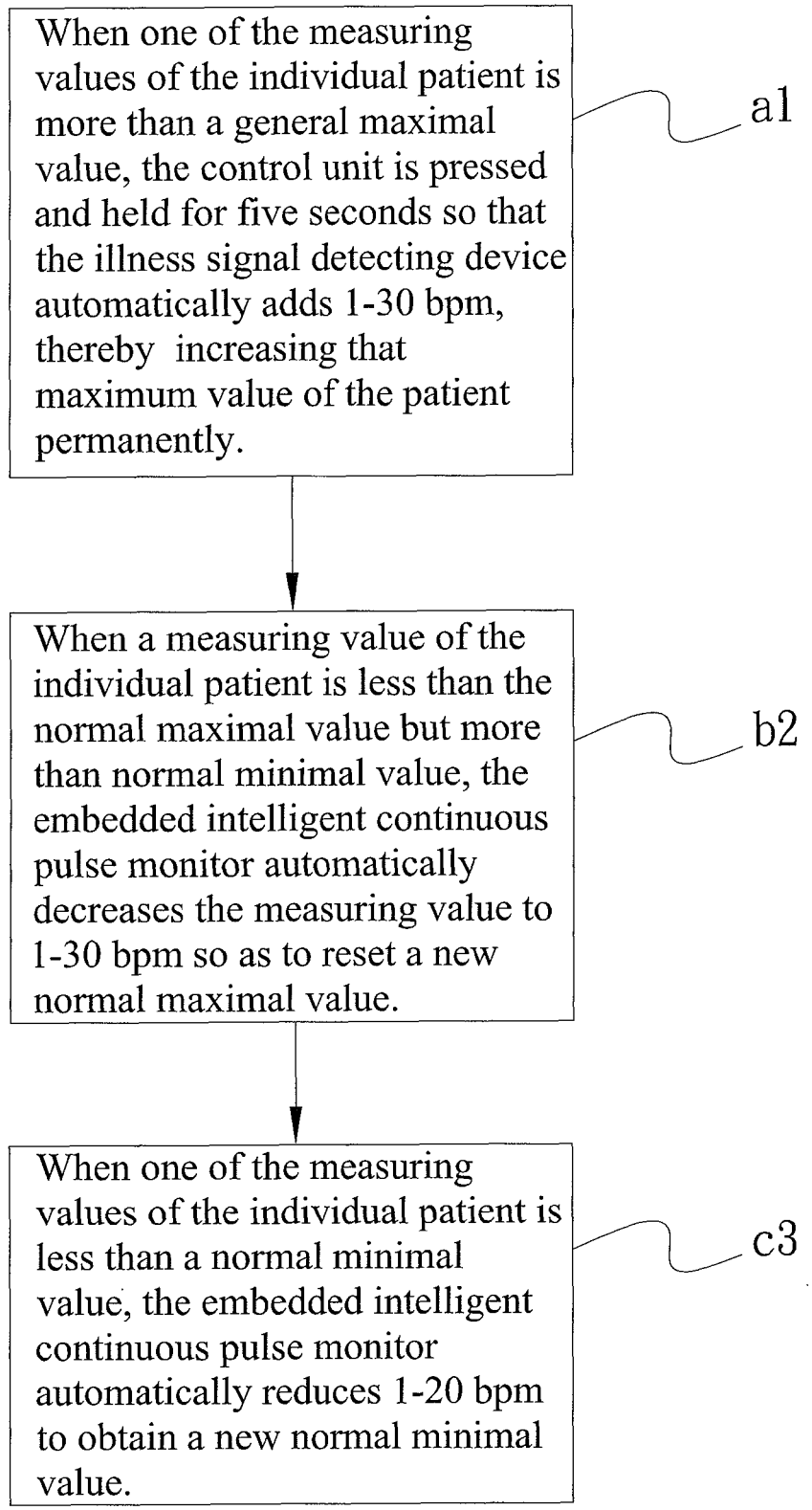
FIG. 4 is a flow chart showing the set steps of the sick signal, embedded intelligent continuous pulse monitor being used to a specific patient.

As illustrated in FIG. 4, a flow chart shows the steps of the sick signal, embedded intelligent continuous pulse monitor 1 being applied to a specific patient as follows, wherein a chip logical flow allows the sick signal, embedded intelligent continuous pulse monitor to be modified to be suitable for the specific patient (with quick or slow heart beating, such as normal variants):

First, the sick signal, embedded intelligent continuous pulse monitor is started by user to be calibrated;

Secondary, as the caregiver finds the patient's status does not match the warning signal (e.g., as the patient feels well but a warning signal is made, or the patient feel sick, such as having a fever, but the warning signal is not made), the control unit 14 is pressed and held for five seconds to automatic adjust the sick signal, embedded intelligent continuous pulse monitor 1 as follows, a1. when one of the normal measuring values of the individual patient is more than a normal maximum value, the control unit 14 is pressed and held for five seconds so that the sick signal, embedded intelligent continuous pulse monitor automatically adds 1-30 bpm to the measuring value to obtain a new normal maximum value.

b2. when a measuring value of the individual patient is less than the normal maximum value but more than normal minimum value, the embedded intelligent continuous pulse monitor automatically decreases the measuring value by 1-30 bpm so as to reset a new normal maximum value.

c3. when one of the measuring values of the individual patient is less than a normal minimum value, the embedded intelligent continuous pulse monitor automatically decreases the measuring value by 1-20 bpm to obtain a new normal minimum value.

Figure 5:
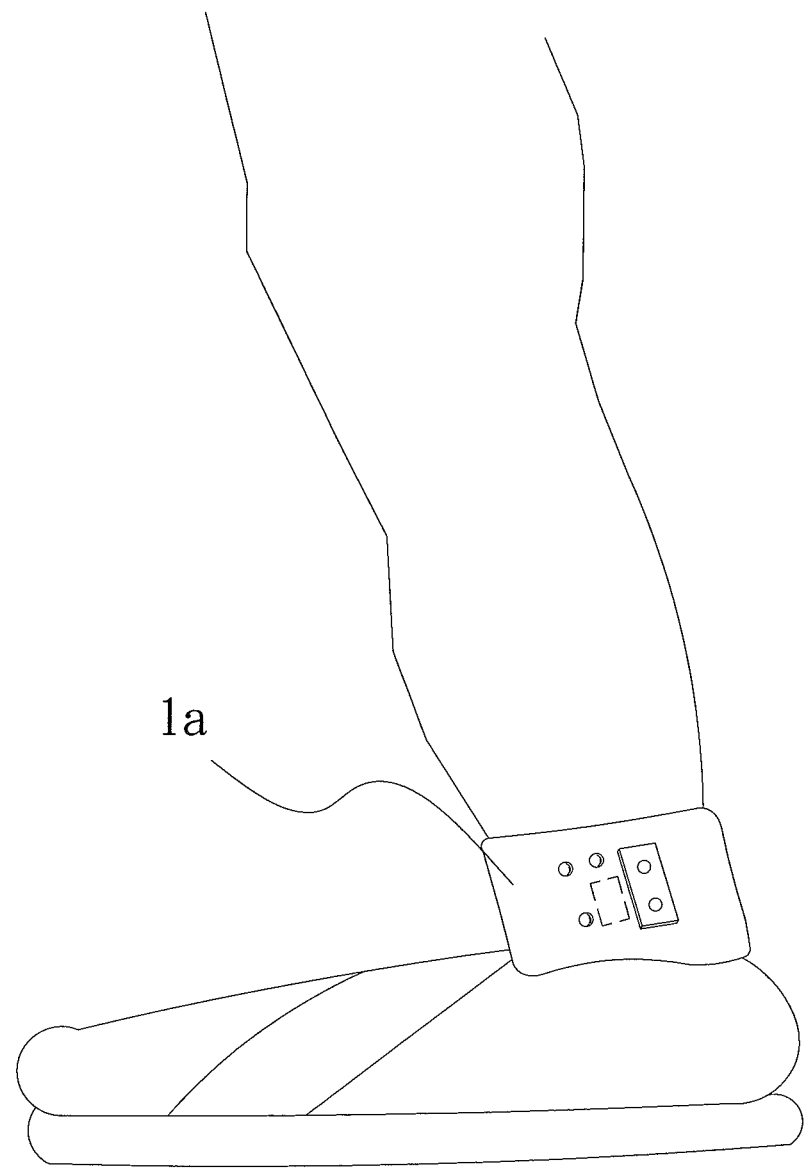
FIG. 5 is a plan showing the operation of another sick signal, embedded intelligent continuous pulse monitor being fitted to a user's ankle.

FIG. 5 shows another ankle type of sick signal, embedded intelligent continuous pulse monitor being used to a specific patient, wherein a sick signal, embedded intelligent continuous pulse monitor 1a is embedded to a flexible material which is fitted to the patient's ankle to sense a pulsing frequency of the patient, and the operating method is set based on above-mentioned processed without further remarks.

While we have shown and described various embodiments in accordance with the present invention, it is clear to those skilled in the art that further embodiments may be made without departing from the scope of the present invention.

What is claimed:

1. A monitoring method of a sick signal, embedded intelligent continuous pulse monitor comprising the steps of:
   1) inputting a patient's age by using a control unit and transmitting data to a processing unit to be read;
   2) calculating measuring values by using the processing unit and comparing the measuring values with a standard value based on a patient's age, wherein when a first measuring value of the patient is more than a normal maximum value, the control unit is pressed and held for five seconds so that the sick signal, embedded intelligent continuous pulse monitor automatically adds 1-30 bpm to said first measuring value to obtain a new normal maximum value; when a second measuring value of the patient is less than said normal maximum value but more than a normal minimum value, the embedded intelligent continuous pulse monitor automatically decreases the second measuring value by 1-30 bpm so as to obtain a reset new normal maximum value; and when a third measuring value of the patient is less than the normal minimum value, the embedded intelligent continuous pulse monitor automatically reduces 1~20 bpm from said third measuring value to obtain a new normal minimum value; and if a further measuring value has a value of 1-30 pulses more than said new normal maximum value or a value of 1-30 pulses less than said new normal minimum value of the patient's age, an alarm signal will be set off;
   3) receiving said alarm signal transmitted from the processing unit and making a warning signal by a display unit;
   4) using the control unit to generate a postponing function as the display unit makes the warning signal; and
   5) transmitting the warning signal to an external device at a remote distance through a signal transmitting unit to be recorded by a medical personnel.

* * * * *